United States Patent [19]

Bjornson

[11] 4,072,713

[45] Feb. 7, 1978

[54] METHOD FOR SEPARATING TETRAALKYLAMMONIUM SALTS

[75] Inventor: Geir Bjornson, Bartlesville, Okla.

[73] Assignee: Phillips Petroleum Company, Bartlesville, Okla.

[21] Appl. No.: 275,546

[22] Filed: July 27, 1972

[51] Int. Cl.² .............................................. C07C 87/32
[52] U.S. Cl. ........................... 260/567.6 M; 204/73 A
[58] Field of Search ................................ 260/567.6 M

[56] References Cited

U.S. PATENT DOCUMENTS

| | | |
|---|---|---|
| 3,267,131 | 8/1966 | Campbell et al. . 204/73A; 260/465.8 |
| 3,280,168 | 10/1966 | Campbell et al. .................. 204/73 A |
| 3,335,162 | 8/1967 | Campbell et al. ............ 260/567.6 M |
| 3,493,597 | 2/1970 | Campbell et al. ............ 260/567.6 M |
| 3,674,653 | 7/1972 | Seko et al. .... 204;260/73 A;465.8 X |

Primary Examiner—Paul M. Coughlan, Jr.
Assistant Examiner—D. B. Springer

[57] ABSTRACT

Apparatus and method for separating tetraalkylammonium salt from a first stream comprising adiponitrile, dissolved tetraalkylammonium salts, and unconverted acrylonitrile discharging from an electrohydrodimerization process by passing the first stream through a distillation zone for separating unconverted acrylonitrile therefrom, mixing aqueous phosphoric acid with the resultant bottoms stream to form an emulsion, and separating the emulsion into an essentially salt-free organic phase and a tetraalkylammonium salt-containing aqueous phase.

7 Claims, 1 Drawing Figure

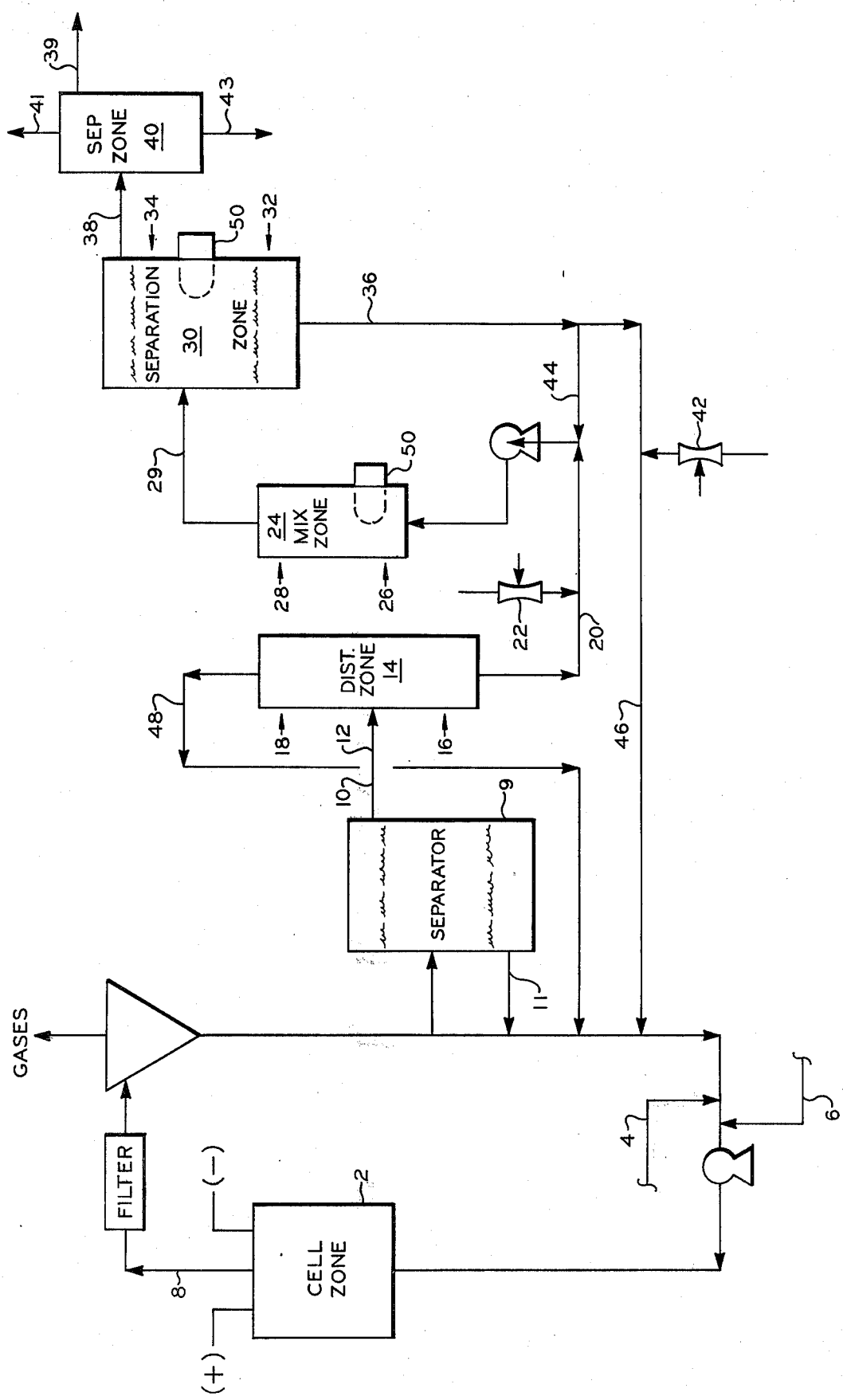

METHOD FOR SEPARATING TETRAALKYLAMMONIUM SALTS

In an electrohydrodimerization process of converting acrylonitrile into adiponitrile which is a valuable precursor in the manufacture of nylon fibers, an aqueous electrolyte comprising a relatively large amount of conducting inorganic salt such as potassium phosphate and a small amount of a directing (catalytic) organic salt such as tetrabutylammonium phosphate, is continuously circulated between two suitable electrodes. Acrylonitrile is continuously added to this circulating system under conditions which provide an emulsion between the two electrodes. As the electrolysis proceeds, a small slip-stream is removed from the circulating emulsion, is allowed to settle, and an organic phase which constitutes the desired first stream comprising adiponitrile, dissolved tetraalkylammonium salts, and unconverted acrylonitrile is drawn off for isolation and further processing.

At least a small amount of salts containing a tetraalkylammonium cation, such as tetrabutylammonium cation, is required to direct the reaction to the desired products. However, the organic nature of this cation imparts some solubility in organic liquids. Consequently, in the circulating emulsion system, the tetraalkylammonium salt distributes itself between the aqueous phase and the organic phase. The fact that the emulsion system contains a relatively large amount of purely inorganic salts contributes to a still greater concentration of the tetraalkylammonium ion in the organic phase by a "salting out" effect. Consequently, when the first stream containing the crude organic product is removed from the separation zone, a small amount of the tetraalkylammonium salt is also removed with it. Because this salt is a relatively costly material, some provision must be made to prevent the salt from being lost to the process.

Ordinarily, one might expect that a simple back-extraction of this crude organic product with water would be adequate to remove the tetraalkylammonium salt. However, efforts to remove the dissolved tetraalkylammonium salts from the organic phase by simple extraction with water were found to be only partially successful. The ordinarily highly extractable tetraalkylammonium salts were found to be only partially extractable when associated with the organic phase from the process effluent.

This problem has been solved by the process of the present invention. It has been found that the tetraalkylammonium salt can be essentially completely recovered and recycled to the electrohydrodimerization process by a sequence of steps which includes a mild treatment with dilute phosphoric acid.

Although the theoretical reason for the success of this invention is not known with certainty, it is believed to be related to the anion of the tetraalkylammonium salt and to the undivided cell type of operation of the preferred electrohydrodimerization process, wherein all of the organics come in contact with the anode as well as with the cathode with some additional anions being generated in the process. Some of these anions, such as the carbonate, cyanide, and anions of weak organic acids, can produce a tetraalkylammonium salt which is much less extractable with water from an organic medium. The treatment with dilute phosphoric acid can convert the tetraalkylammonium salts to the tetraalkylammonium phosphate salts which can then be more easily extracted with water from an organic medium.

This invention therefore resides in apparatus and method for separating tetraalkylammonium salt from a first stream comprising adiponitrile, dissolved tetraalkylammonium salts, and unconverted acrylonitrile discharging from an electrohydrodimerization process by passing the first stream through a distillation zone for separating unconverted acrylonitrile therefrom, mixing aqueous phosphoric acid with the resultant bottoms stream to form an emulsion, and separating the emulsion into an essentially salt-free organic phase and a tetraalkylammonium salt-containing aqueous phase.

Other aspects, objects, and advantages of the present invention will become apparent from a study of the disclosure, the appended claims, and the drawing.

The drawing is a diagrammatic view of the apparatus of this invention.

Referring to the drawing, an electrohydrodimerization cell 2 is connected to means for controllably passing an acrylonitrile feed stream 4 and a make-up tetraalkylammonium salt stream 6 thereinto. An aqueous electrolyte comprising a relatively large amount of conducting inorganic salt such as a potassium phosphate and a small amount of a directing (catalytic) organic salt such as a tetrabutylammonium phosphate is circulated through the cell 2 which has two suitable electrodes. As electrolysis occurs, as known in the art, a stream 8 is removed from the cell zone, is filtered, de-gassed, allowed to settle in separator 9, and a first stream 10 comprising adiponitrile, dissolved salts, and unconverted acrylonitrile is recovered as an organic phase. An aqueous phase is returned, via line 11, to the recirculating reaction mixture.

The first stream is passed via line 12 into a distillation column 14. The distillation column 14 has first and second end portions 16, 18. A bottoms product conduit 20 is connected to the first end portion 16 of the distillation column 14 for passing a bottoms product stream from the distillation column 14. A first means, such as an injector 22, is associated with the bottoms product stream for controllably adding acid thereto. A second means, such as a packed mixing column 24 having first and second end portions 26, 28 for example, is connected at its first end portion 26 to the bottoms product conduit 20 at a location downstream of the injector 22 for receiving the resultant acid-treated bottoms product stream and mixing said stream during the passage therethrough to form an emulsion which is discharged from the second end portion 28 of said mixing means 24.

The emulsion is passed via line 29 into a separation column 30 which has first and second end portions 32, 34. In the separation column 30, the emulsion is separated, preferably by gravity settling, into a salt-containing aqueous phase which is discharged from the first end portion 32 of the column 30 via line 36 and an adiponitrile-containing product stream which is discharged from the second end portion 34 of the column 30 via line 38.

A separating zone 40 is connected to line 38 for receiving the adiponitrile-containing product stream and separating the adiponitrile therefrom. Adiponitrile, light by-products, and heavy by-products leave separation zone 40 via lines 39, 41, and 43, respectively.

In order to conserve valuable salts in the process, it is preferred that a line 44 be connected to line 36 and line 20 for recycling a portion of the separated aqueous phase from the decantation column 30 to the mixing column 24 and a line 46 be connected to line 36 and the cell 2 for passing a portion of the separated aqueous phase from the decantation column 30 to the emulsion circulating through said cell 2.

It is recommended that a second injector 42 be associated with line 46 for controllably injecting material such as potassium hydroxide or sodium hydroxide, for example, to adjust the pH of the stream to a preselected level, for example a pH of 7.5. A line 48 is connected from the second end portion 18 of the distillation column 14 and to the emulsion stream circulating through cell zone 2 for passing an overhead stream from the distillation column to the cell. This overhead stream comprises separated water and unconverted acrylonitrile.

In the method of this invention, a crude organic phase, which contains small amounts of dissolved organic and inorganic salts, is continuously fed into a distillation zone 14 via line 12. The crude organic phase product from any suitable process which employs tetraalkylammonium phosphate salts can be used, although processes utilizing an undivided cell and an emulsified recirculating reaction medium containing minor amounts of tetraalkylammonium phosphate salts and substantial amounts of alkali metal phosphate salts are presently most applicable. This crude organic product will typically contain major amounts of adiponitrile product and unconverted acrylonitrile, and smaller amounts of other nitriles such as propionitrile and other higher molecular weight nitriles. Additionally, such a crude organic product will generally contain a finite amount but less than about 15 weight percent, generally less than 10 weight percent, dissolved water and less than about 5 weight percent, generally less than 3 weight percent, dissolved tetraalkylammonium salt. Very minor amounts of other purely inorganic salts can also be present.

The tetraalkylammonium phosphate salts which are particularly applicable to the present process are those wherein each alkyl group contains 1-20 carbon atoms and wherein the total number of all the carbon atoms in all the alkyl groups is 11-25. Some examples are tripropylbutylammonium phosphate, tetrabutylammonium phosphate, tributyloctylammonium phosphate, and the like, and mixtures thereof.

In the distillation zone 14, which is preferably operated under vacuum distillation conditions with overhead temperatures of 75° to 90° F to minimize decomposition of the materials passing through it, at least 90 percent, preferably at least 95 percent, of the unconverted acrylonitrile is removed as an overhead product. Any dissolved water present will also be contained in the overhead. Any suitable distillation apparatus or combinations of distillation means can also be used to effect this separation. The mixture of water and acrylonitrile is returned to the electrohydrodimerization process via line 48. The bottoms product stream from distillation zone 14, which contains the principal organic product as well as the tetraalkylammonium salts, is moved to the phosphoric acid treatment and mixing zone.

The crude organic product, which is now substantially free of water and unconverted acrylonitrile, is treated with a dilute aqueous solution of orthophosphoric acid which enters the process through means 22. The amount of phosphoric acid added to the process at this point will, of course, vary with the amount of tetraalkylammonium cation present in the stream. Generally, sufficient phosphoric acid will be added, such as an amount chemically equivalent with the tetraalkylammonium cation to insure that all the tetraalkylammonium salt is in the form of a water-extractable phosphate salt. Quantities several times that stoichiometrically required can generally be used. The phosphoric acid is added as a dilute aqueous solution and the amount of water can vary accordingly to the requirements of the electrohydrodimerization process which consumes water. Ordinarily, 1-5 weight percent solutions of orthophosphoric acid are satisfactory. Any suitable means or apparatus for injecting the aqueous acid into the organic stream can be used.

The phosphoric acid-treated organic stream is then passed into the mixing zone 24. Any suitable apparatus for mixing, preferably a packed column, can be used for this purpose. In mixing zone 24, the aqueous phosphoric acid solution is mixed with the salt-containing organic stream thus forming an emulsion. This emulsion is then conducted to a decantation zone 30 via line 29.

A stream of essentially salt-free adiponitrile and organic by-products is removed from decantation zone 30 through line 38. Line 38 leads to separation zone 40 for separation and recovery of adiponitrile product.

The aqueous phase leaves decantation zone 30 through line 36 and is preferably recirculated through mixing zone 24 by means of line 44. However, a portion of the aqueous phase from decantation zone 30 is preferably passed via line 36 and line 46 to the recirculating electrolyte system of the electrohydrodimerization cell zone 2. Prior to its return to the cell zone, the aqueous solution of tetraalkylammonium salts is preferably treated with sufficient base such as potassium hydroxide via means 42 to adjust the pH of the aqueous stream to the desired level. This pH level is essentially that desired in the electrohydrodimerization cell 2, and is generally in the range of pH 6 to pH 12.

The operation of the present invention is illustrated in the following calculated example. The units are in pounds per hour. The stream numbers refer to the drawing.

EXAMPLE

A crude organic phase which has been separated from the effluent from an acrylonitrile electrohydrodimerization process enters distillation unit through line 12. The composition and flow rates of the contents of line 12 are as follows:

| Adiponitrile | 90 lbs per hr |
|---|---|
| Acrylonitrile | 50 lbs per hr |
| Other nitrile by-products* | 10 lbs per hr |
| Water | 5 lbs per hr |
| Tetrabutylammonium ion | 0.8 lb per hr |

*Propionitrile, biscyanoethyl ether, 2-cyanoethyladiponitrile, etc.

Distillation unit 14 operating under reduced pressure sufficient to maintain a head temperature of 85° F. discharges an overhead stream 48 as follows:

| Water | 5 lbs per hr |
|---|---|
| Acrylonitrile | 49 lbs per hr |

The overhead stream 48 is recycled to the cell zone of the electrohydrodimerization process. The underflow from distillation unit 14 is mixed with approximately 20 lbs per hour water and approximately 0.8 lb per hour of 85% $H_3PO_4$. This mixture is passed into the stream being circulated between mixing column 24 and separation column 30.

The separation column 30 discharges an organic phase through line 38 as follows:

| Adiponitrile | 90 lbs per hr |
|---|---|
| Acrylonitrile | 1 lb per hr |
| Other nitriles | 10 lbs per hr |
| Organic and inorganic salts | Substantially none |

Line 38 leads to separating zone 40 at which location adiponitrile product is separated and recovered.

The decantation column 30 also discharges a lower aqueous phase through line 36 of which a major portion is recirculated to mixing column 24 via line 44 and a minor portion is recycled back to the electrohydrodimerization cell zone 2 via line 46. Prior to return to the cell, the aqueous phase in line 46 is treated with sufficient potassium hydroxide via injector 42 to adjust the pH to about 7.5. Line 46, being recycled to the electrohydrodimerization cell zone carries 22.2 lbs per hour water and 0.8 lb per hour tetrabutylammonium ion.

Other modifications and alterations of this invention will become apparent to those skilled in the art from the foregoing discussion, example, and accompanying drawing, and it should be understood that this invention is not to be unduly limited thereto.

What is claimed is:

1. In a process for the production of adiponitrile wherein acrylonitrile, an aqueous electrolyte, and a tetraalkylammonium salt, each of the alkyl radicals of which has 1–20 carbon atoms and the tetraalkylammonium has 11–25 carbon atoms, are subjected to an electrolysis in an electrohydrodimerization cell, and wherein the adiponitrile formed is recovered from a first emulsion coming from said cell, the improvement which comprises separating said first emulsion to form a first organic and a first aqueous phase, distilling said first organic phase to remove acrylonitrile therefrom, mixing the remaining first organic phase with phosphoric acid to form a second emulsion, separating said second emulsion into a second aqueous and a second organic phase, and recovering the adiponitrile from the organic phase and the aqueous phase comprising the tetraalkylammonium phosphate salt.

2. A process in accordance with claim 1 wherein an aqueous phosphoric acid comprising about 1 to about 5 weight percent phosphoric acid is mixed with the remaining first organic phase to form said second emulsion.

3. A process in accordance with claim 1 wherein the volume of phosphoric acid added is an amount greater than stoichiometric, required to react said phosphoric acid with said tetraalkylammonium salt of said remaining first organic phase.

4. A process in accordance with claim 1 wherein said phosphoric acid and said remaining first organic phase are mixed by passing said material together through a packed column.

5. A process in accordance with claim 1 wherein a portion of the recovered second aqueous phase is recycled to the electrohydrodimerization cell.

6. A process in accordance with claim 1 wherein at least a portion of the acrylonitrile separated in said distillation step is passed to an electrohydrodimerization cell.

7. A process in accordance with claim 1 wherein the recovered aqueous phase is mixed with a sufficient quantity of a base to adjust the pH of the second aqueous phase to a value in the range of 6 to 12 and wherein the resulting second aqueous phase is passed into an electrohydrodimerization cell.

* * * * *